| (12) | United States Patent | (10) Patent No.: | US 7,140,368 B1 |
|---|---|---|---|
| | Collins | (45) Date of Patent: | Nov. 28, 2006 |

(54) LARYNGEAL MASK AIRWAY

(75) Inventor: Michael Norman Collins, Folkestone (GB)

(73) Assignee: Smiths Group PLC, London (GB)

( * ) Notice: Subject to any disclaimer, the term of this patent is extended or adjusted under 35 U.S.C. 154(b) by 640 days.

(21) Appl. No.: 10/031,609

(22) PCT Filed: Aug. 7, 2000

(86) PCT No.: PCT/GB00/03045

§ 371 (c)(1),
(2), (4) Date: Jan. 22, 2002

(87) PCT Pub. No.: WO01/13980

PCT Pub. Date: Mar. 1, 2001

(30) Foreign Application Priority Data

Aug. 26, 1999 (GB) .................................. 9920098.2

(51) Int. Cl.
*A61M 16/00* (2006.01)

(52) U.S. Cl. .............................. 128/207.14; 128/207.15

(58) Field of Classification Search ........... 128/207.11, 128/207.15, 200.26, DIG. 26
See application file for complete search history.

(56) References Cited

U.S. PATENT DOCUMENTS

| 4,509,514 | A | * | 4/1985 | Brain | 128/207.15 |
|---|---|---|---|---|---|
| 4,995,388 | A | * | 2/1991 | Brain | 128/207.15 |
| 5,249,571 | A | * | 10/1993 | Brain | 128/207.14 |
| 5,303,697 | A | * | 4/1994 | Brain | 128/200.26 |
| 5,305,743 | A | * | 4/1994 | Brain | 128/207.15 |
| 5,355,879 | A | * | 10/1994 | Brain | 128/207.15 |
| 5,391,248 | A | * | 2/1995 | Brain | 156/242 |
| 5,632,271 | A | * | 5/1997 | Brain | 128/207.15 |
| 5,682,880 | A | * | 11/1997 | Brain | 128/207.15 |
| 5,771,889 | A | * | 6/1998 | Pagan | 128/207.15 |
| 5,791,341 | A | * | 8/1998 | Bullard | 128/207.15 |
| 5,878,745 | A | * | 3/1999 | Brain | 128/207.15 |
| 5,881,726 | A | * | 3/1999 | Neame | 128/207.15 |
| 5,896,858 | A | * | 4/1999 | Brain | 128/207.15 |
| 5,979,445 | A | * | 11/1999 | Neame et al. | 128/207.15 |
| 5,983,897 | A | * | 11/1999 | Pagan | 128/207.15 |
| 6,116,243 | A | * | 9/2000 | Pagan | 128/207.15 |
| 6,422,239 | B1 | * | 7/2002 | Cook | 128/207.15 |

* cited by examiner

*Primary Examiner*—Anhtuan T. Nguyen
*Assistant Examiner*—Darwin P. Erezo
(74) *Attorney, Agent, or Firm*—Louis Woo

(57) ABSTRACT

A laryngeal mask airway has a main tubular shaft (1) with a mask portion (5) attached at its patient end (3). The mask portion (5) comprises a mount (50) and a sealing cuff (60) attached to the mount. The interior of the mount (50) defines a large volume atrium (54) communicating with the bore of the shaft (1) at one end and with an opening (61) through the cuff (60) at its other end. The join between the shaft (1) and the mount (50) is located above the rear part (63) of the cuff (60). The height of the atrium (54) is between 2.5 and 3.5 the internal diameter of the shaft. The volume of the atrium (54) is such that the ratio of the internal diameter of the shaft cubed to the internal volume of the atrium is between 50 and 68.

9 Claims, 3 Drawing Sheets

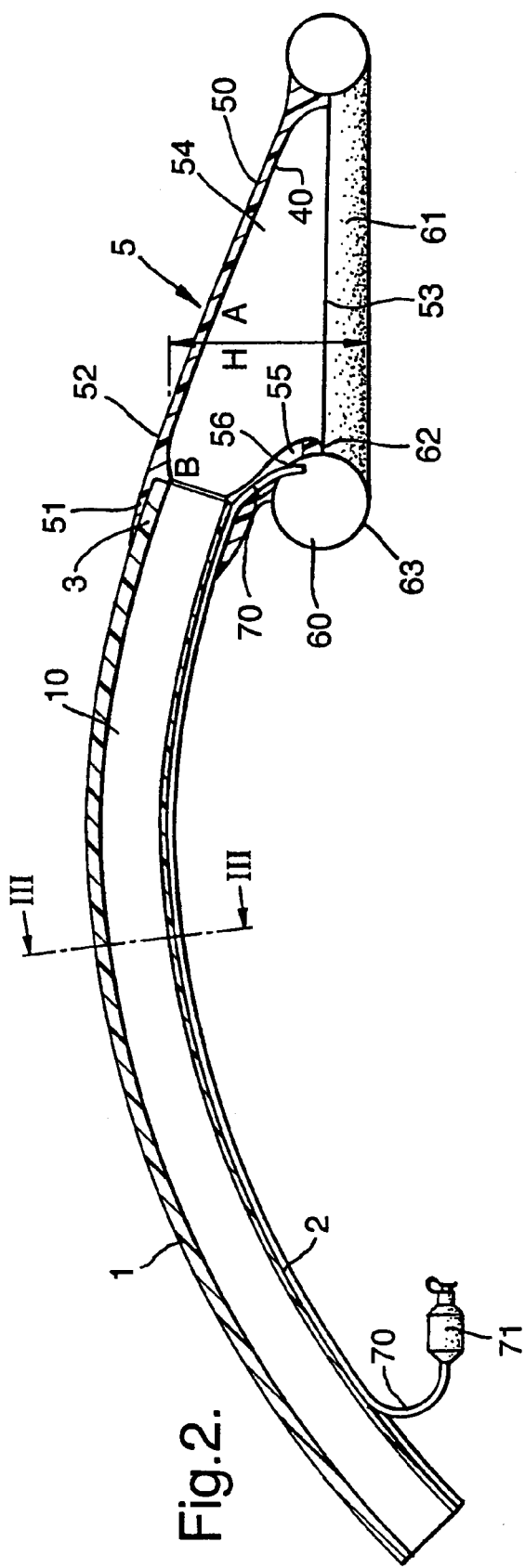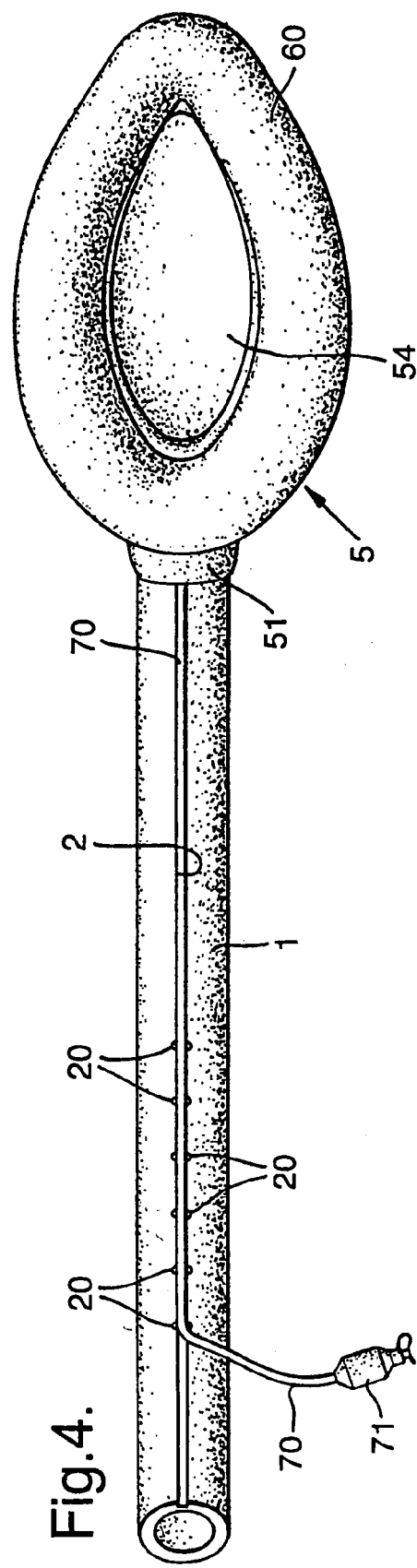
Fig.2.
Fig.4.

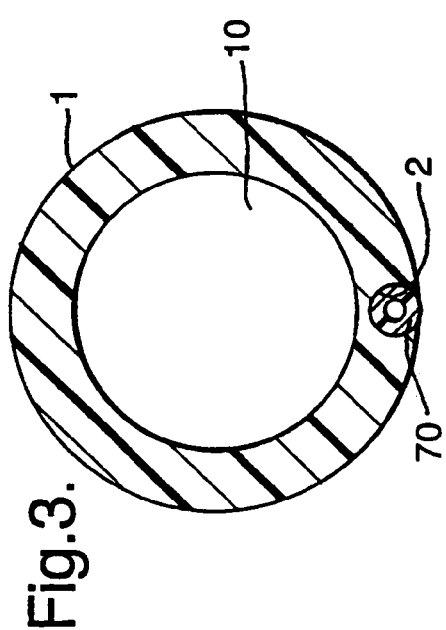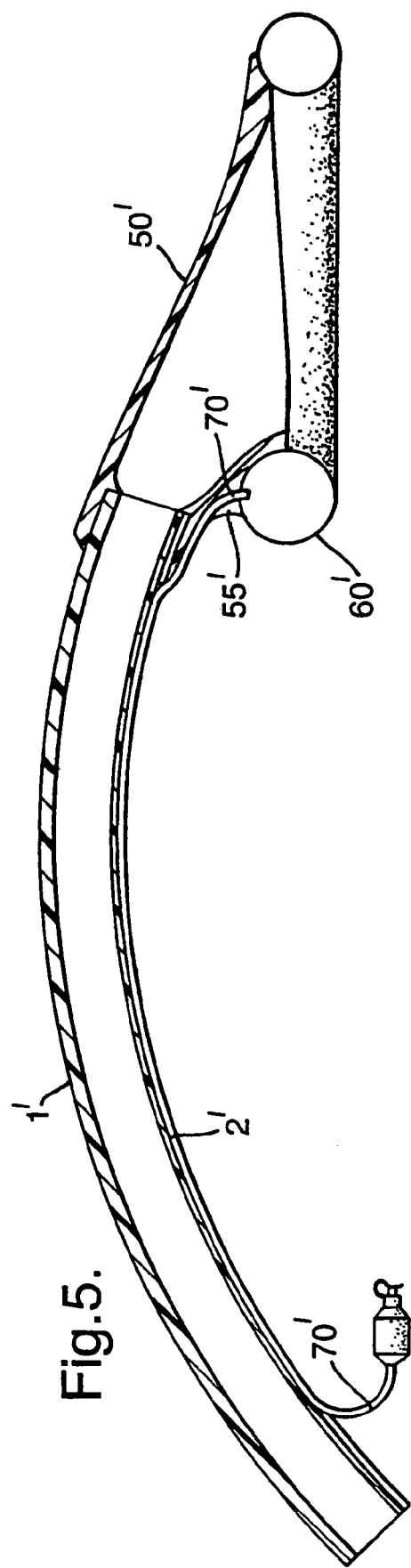

LARYNGEAL MASK AIRWAY

FIELD OF THE INVENTION

This invention relates to apparatus in the form of a laryngeal mask airway including a tubular portion and a mask portion at its patient end having a sealing cuff of generally oval shape defining an opening within its centre and adapted to seal with patient tissue around the larnygeal inlet, the mask portion defining a recess extending from the opening to the patient end of the tubular portion.

BACKGROUND OF THE INVENTION

Laryngeal mask airways are used to ventilate and to supply anaesthetic gas to a patient during surgery. Laryngeal mask airways differ from endotracheal tubes, which extend into the trachea and terminate beyond the vocal folds. By contrast, laryngeal mask airways have a tubular shaft opening into the centre of a generally elliptical mask or cuff, which is inflated to seal in the region of the hypopharnyx, at the top of the trachea. The cuff is inflated with air supplied along a small-bore inflation line communicating with the interior of the cuff. Laryngeal masks are described in, for example: U.S. Pat. No. 5,355,879, U.S. Pat. No. 5,305,743, U.S. Pat. No. 5,297,547, U.S. Pat. No. 5,282,464, GB 2267034, U.S. Pat. No. 5,249,571, U.S. Pat. No. 5,241,956, U.S. Pat. No. 5,303,697, GB 2317830, GB 2249959, GB 2111394, EP 448878, U.S. Pat. No. 4,995,388, GB 2205499, GB 2128561, GB 2298797, GB 2321854, GB 2334215, GB 2323289, GB 2323290, GB 2318735 and GB 2330312.

One problem with laryngeal masks is that there is a risk that the air passage along the mask may be blocked by the epiglottis during insertion. Attempts have been made to reduce this risk by means of bars extending across the opening to the mask but this has the disadvantage of making it more difficult to insert instruments along the airway.

It is an object of the present invention to provide alternative medico-surgical apparatus.

BRIEF SUMMARY OF INVENTION

According to one aspect of the present invention there is provided apparatus of the above-specified kind, characterised in that the patient end of the tubular portion is located above and to the rear of the rear side of the opening such as to space it away from the epiglottis.

The patient end of the tubular portion is preferably located substantially midway across the width of the rear side of the sealing cuff. The tubular portion may be a separate tube bonded into a collar on the mask portion. The longitudinal centre line along the internal surface of the roof of the recess is preferably substantially straight. The height of the recess may be between 2.5 and 3.5 the internal diameter of the tubular portion. The ratio of the internal diameter of the tubular portion cubed to the volume of the recess is preferably between 50 and 68.

According to another aspect of the present invention there is provided a laryngeal mask airway including a tubular portion and a mask portion at its patient end having a sealing cuff of generally oval shape defining an opening within its centre and adapted to seal with patient tissue around the larnygeal inlet; the mask portion defining a recess extending from the opening to the patient end of the tubular portion, characterised in that the height of the recess is between 2.5 and 3.5 the internal diameter of the tubular portion.

The height of the recess is preferably between 2.96 and 3.27 the internal diameter of the tubular portion.

According to a further aspect of the present invention there is provided a laryngeal mask airway including a tubular portion and a mask portion at its patient end having a sealing cuff of generally oval shape defining an opening within its centre and adapted to seal with patient tissue around the larnygeal inlet, the mask portion defining a recess extending from the opening to the patient end of the tubular portion, characterised in that the ratio of the internal diameter of the tubular portion cubed to the volume of the recess is between 50 and 68.

Preferably, the ratio of the internal diameter of the tubular portion cubed to the internal volume of the recess is between 50 and 60.

DETAILED DESCRIPTION OF DRAWINGS

A medico-surgical tube in the form of a laryngeal mask airway according to the present invention, will now be described, by way of example, with reference to the accompanying drawings, in which:

FIG. 2 is a sectional side elevation view of the airway;

FIG. 3 is a transverse section across the airway along the line III—III of FIG. 2 to an enlarged scale;

FIG. 4 is a view of the airway from below; and

FIG. 5 is a sectional side elevation view of an alternative airway.

DETAILED DESCRIPTION OF THE INVENTION

Figure 1:
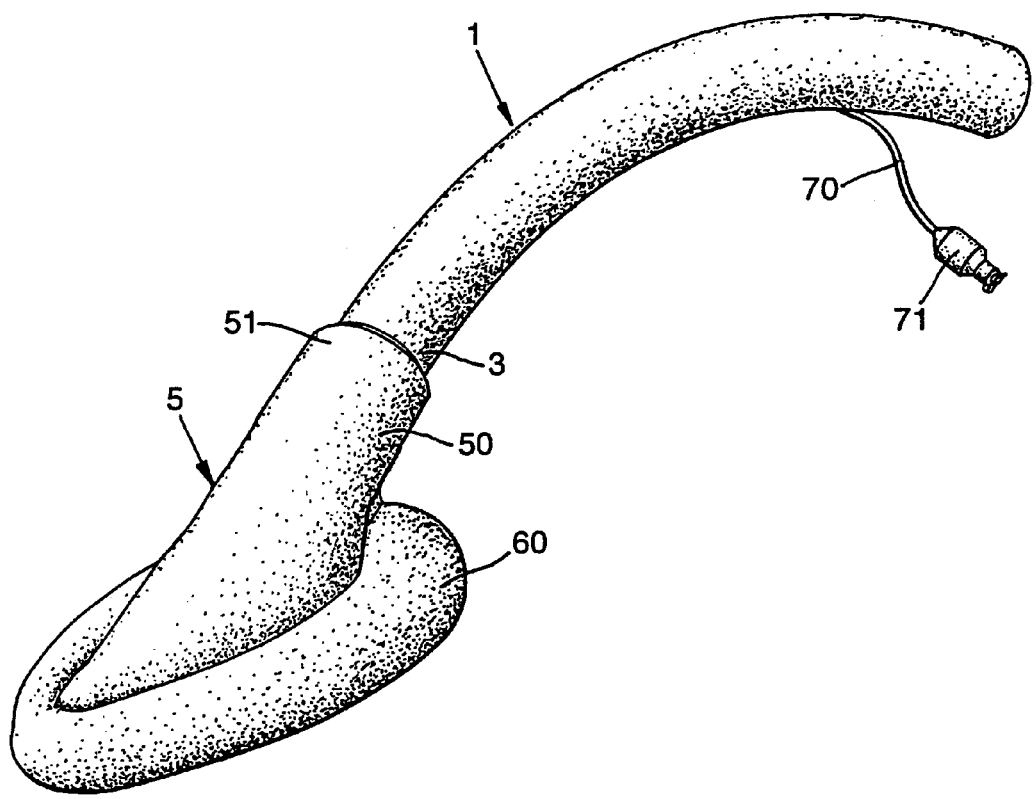
FIG. 1 is a perspective view of the airway.

With reference to FIGS. 1 to 4, the airway includes a curved tube or shaft 1 of a bendable plastics material having a channel 2 in the form of a groove extending along its length on its outside surface and on the inside of its curve. The shaft 1 is preferably made by extrusion and may be reinforced by means of an embedded helical element, such as of metal or plastics. At its patient end 3, the shaft 1 is attached to a mask portion 5.

The mask portion 5 comprises a mount member 50 of a relatively stiff but compliant plastics material and an inflatable cuff 60 attached to the mount member. The mount member 50 is hollow and of generally shoe shape, having a tubular extension or collar 51 at its upper or posterior side located at the rear, left-hand or machine end of the mount. The patient end 3 of the shaft 1 is bonded into one end of the collar 51. The other end of the collar 51 opens into a central recess or atrium 54 within the mount 50. The internal, anterior surface of the roof 40 of the atrium 54 is arched transversely but is substantially straight, or is slightly concave, along its longitudinal centre line. The roof 40 is uninterrupted by any surface projections or formations that would impede free movement of the epiglottis over the roof. Viewed in plan, the mount 50 is oval with its lower or anterior side 53 lying on a flat plane extending at an angle of about 30° to the axis of the patient end 3 of the collar 51. A channel 55 in the form of a groove extends along the inside of the mount member 50 in line with the groove 2 along the shaft 1 and this opens through a hole 56 into the cuff 60.

The cuff 60 may be of any conventional form, such as described in GB 2323291 or GB 2321854. The cuff 60 is only shown schematically in the drawings but is of annular, elliptical shape, being attached to the forward end surface 53 of the mount member 50 and having a central opening 61 into the atrium 54. The cuff 60 is of a thin, flexible plastics material so that it can be deflated to a low profile for insertion and can be inflated to seal with surrounding tissue when correctly positioned.

The roof 40 of the mount 50 is relatively high compared with previous laryngeal mask airways, especially its central region A and its rear region B adjacent the tubular portion or collar 51. The height H of the atrium ranges from about 2.5 to 3.5 times the internal diameter ID of the shaft 1, or its equivalent where the shaft does not have a circular section— preferably the ratio H/ID is between 2.96 and 3.27. In this way, the atrium 54 has a relatively large volume compared with previous airways. In particular, the ratio of $ID^3$/Volume is in the range 50 to 68 where Volume is the volume of the atrium 54 defined by a plane of the lower, sealing surface of the cuff 61 when inflated, and a vertical, transverse surface through the highest point of the rear region B. For a typical tube having an internal diameter of 8.5 mm, the ratio H/ID might be 3.06 and the ratio of $ID^3$/Volume might be 61.82.

The smallest part of the atrium 54, where the patient end of the collar 51 opens into the atrium, is the part most likely to be blocked by the epiglottis during insertion. The collar 51 positions the patient end 3 of the shaft 1 to the rear of the rear part 62 of the opening 61 and, more particularly, positions it directly above the rear part 63 of the cuff 60 so that it is located as far away as possible from the epiglottis, thereby minimizing the risk of blockage. The large volume of the atrium 54 also ensures that the epiglottis can move freely within the mask, should it enter, so that there is less risk of it catching on the interior of the mask. The present construction avoids the need for any obstruction across the opening of the mask in order to prevent blockage by the epiglottis.

In general, the patient end of the tubular portion 1 is located to the rear of the rear side 62 of the opening 61, that is, on the side towards the machine end of the airway, and is preferably located approximately midway across the width of the sealing cuff. Instead of the tube and mount being separate components, they could be provided by one integral moulded component, with the location where the tubular portion increases in internal diameter being regarded as the patient end of the tubular portion.

The airway also includes an inflation line 70 in the form of a small-diameter flexible plastics tube extending along the groove 2 in the shaft 1, with the patient end of the tube extending along the groove 55 in the mount member 50 and projecting through the hole 56 into the cuff 60. The cuff 60 is sealed with the outside of the inflation line 70 so that it opens into the interior of the cuff. The rear, machine end of the inflation line 70 is attached to a combined inflation indicator balloon and connector 71 of conventional kind. The groove 2 in section forms the major part of a circle, being open on the surface of the shaft through a slit so that the inflation line 70 is retained in the groove mechanically, although it is preferably also bonded into the groove close to the patient end of the shaft 1, such as by means of a solvent or adhesive. A number of lateral notches 20 are spaced from one another along the machine end of the groove 2. The size of the notches 20 is such as to allow the inflation line 70 to extend out of the groove 2 through a notch. The airway is supplied with the inflation line 70 extending out of the groove 2 through the notch 20 closest to the machine end of the shaft 1. If the user wishes to cut the shaft 1 shorter, at a location forwardly of where the inflation line 70 extends from the shaft, he simply pulls the inflation line away from the shaft so that it peels out of the groove 2 to the next notch 20, or to any other notch, thereby reducing the length of the inflation line attached with the shaft. In this way, the inflation line 70 is kept neatly with the shaft along most of the length of the shaft 1 but the shaft can be cut to any desired length. There are other ways in which the inflation line could be attached with the shaft, such as by means of a rupturable adhesive or other bond. It will be appreciated that this form of peelable attachment of a small-bore line could have applications in other tubes having a minor lumen and where it is desirable to be able to alter the length of the small-bore line attached with the main shaft, such as endotracheal tubes.

Securing the inflation line 70 to the shaft 1 along most of its length avoids any loose tube within the patient's mouth and ensures that the inflation indicator and connector 71 are readily accessible outside the mouth. Reliable assembly of the airway is facilitated by this arrangement compared with alternative arrangements employing an extruded small-bore lumen within the wall of the shaft since, in such arrangements, connection needs to be made to both ends of the bore. The present invention can also be used with shafts that are reinforced.

It is not essential that the channel in the mount member extend along its inner surface; it could extend along an outer surface, as shown in FIG. 5, where similar features to those in FIGS. 1 to 4 are given the same numbers with the addition of a prime'. In this arrangement, the groove 55' extends along the outside of the mount member 50' so that the inflation line 70' can run along the groove and open into the cuff 60'.

The invention claimed is:

1. A laryngeal mask airway consisting of a tubular portion and a mask portion at a patient end of the tubular portion having an inflatable sealing cuff of generally oval shape with no partition therein defining an opening within a center thereof and adapted to seal with patient tissue around the laryngeal inlet, the mask portion defining a chamber extending from the opening to the patient end of the tubular portion where the tubular portion opens directly into the chamber such that the entire chamber is available for receiving patient tissue, characterized in that the patient end of the tubular portion is located above and to the rear of the rear side of the opening such as to space it away from the epiglottis.

2. An airway according to claim 1, characterized in that the patient end of the tubular portion is located substantially midway across the width of the rear side of the sealing cuff.

3. An airway according to claim 1, characterized in that the tubular portion is a separate tube bonded into a collar on the mask portion.

4. An airway according to claim 1, wherein the chamber has a roof, characterized in that the longitudinal center line along the internal surface of the roof of the chamber is substantially straight.

5. An airway according to claim 1, characterized in that the height of the chamber is between 2.5 and 3.5 the internal diameter of the tubular portion.

6. An airway according to claim 1, wherein the chamber has a volume, characterized in that the ratio of the internal diameter of the tubular portion cubed to the volume of the chamber is between 50 and 68.

7. An airway according to claim 2, characterized in that the tubular portion is a separate tube bonded into a collar on the mask portion.

8. A laryngeal mask airway consisting of a tubular portion and a mask portion at a patient end having an inflatable sealing cuff of generally oval shape with no partition therein defining an opening within a center thereof and adapted to seal with patient tissue around the laryngeal inlet, the mask portion defining a chamber whereto the patient end of the tubular portion opens directly into, characterized in that the height of the chamber available for receiving patient tissue is between 2.5 and 3.5 the internal diameter of the tubular portion, and characterized in that the patient end of the tubular portion is located above and to the rear of the rear side of the opening such as to space it away from the epiglottis.

9. An airway according to claim 7, characterized in that the height of the chamber is between 2.96 and 3.27 the internal diameter of the tubular portion.

* * * * *